(12) United States Patent
Greene

(10) Patent No.: US 10,987,284 B2
(45) Date of Patent: Apr. 27, 2021

(54) VOLUME BOOSTING MOLDING HAIR COLORING CREME FORMULATION

(71) Applicant: Michael V. Greene, Colts Neck, NJ (US)

(72) Inventor: Michael V. Greene, Colts Neck, NJ (US)

(*) Notice: Subject to any disclaimer, the term of this patent is extended or adjusted under 35 U.S.C. 154(b) by 353 days.

(21) Appl. No.: 14/545,925

(22) Filed: Jul. 8, 2015

(65) Prior Publication Data

US 2016/0008264 A1 Jan. 14, 2016

Related U.S. Application Data

(60) Provisional application No. 61/999,007, filed on Jul. 14, 2014, provisional application No. 61/999,009, filed on Jul. 14, 2014.

(51) Int. Cl.

| | |
|---|---|
| *A61K 8/97* | (2017.01) |
| *A61K 8/44* | (2006.01) |
| *A61K 8/81* | (2006.01) |
| *A61K 8/37* | (2006.01) |
| *A61K 8/64* | (2006.01) |
| *A61K 8/49* | (2006.01) |
| *A61K 8/34* | (2006.01) |
| *A61K 8/02* | (2006.01) |
| *A61Q 7/00* | (2006.01) |
| *A61K 8/25* | (2006.01) |
| *A61K 8/60* | (2006.01) |
| *A61K 8/92* | (2006.01) |
| *A61K 8/36* | (2006.01) |
| *A61K 8/41* | (2006.01) |
| *A61K 8/31* | (2006.01) |
| *A61Q 5/06* | (2006.01) |
| *A61K 8/9789* | (2017.01) |
| *A61K 8/9794* | (2017.01) |

(52) U.S. Cl.
CPC ............ *A61K 8/022* (2013.01); *A61K 8/4953* (2013.01); *A61K 8/9789* (2017.08); *A61K 8/9794* (2017.08); *A61Q 5/065* (2013.01); *A61Q 7/00* (2013.01)

(58) Field of Classification Search
None
See application file for complete search history.

(56) References Cited

U.S. PATENT DOCUMENTS

| | | | |
|---|---|---|---|
| 3,811,830 A | 5/1974 | Demarco ........................... 8/405 |
| 4,898,595 A | 2/1990 | Fridd et al. ....................... 8/405 |
| 5,112,359 A | 5/1992 | Murphy et al. ................... 8/405 |
| 5,436,010 A | 7/1995 | Lau et al. ...................... 424/450 |
| 5,747,016 A | 5/1998 | Yui et al. ....................... 424/401 |
| 6,110,474 A | 8/2000 | Roman .......................... 424/401 |
| 6,132,704 A | 10/2000 | Bhatt et al. ................... 424/70.1 |
| 6,194,514 B1* | 2/2001 | Scheuermann ....... C08F 265/06 524/558 |
| 6,274,129 B1 | 8/2001 | Bhatt et al. ................. 424/70.11 |
| 6,627,183 B1 | 9/2003 | Young et al. ................. 424/70.1 |
| 8,002,849 B2 | 8/2011 | Prem et al. ....................... 8/405 |
| 8,585,777 B2 | 11/2013 | Misu et al. ....................... 8/405 |
| 8,585,779 B2 | 11/2013 | Sabelle et al. .................... 8/405 |
| 2002/0034485 A1 | 3/2002 | Noser et al. .................. 424/70.1 |
| 2004/0115152 A1* | 6/2004 | Hannich ................... A61K 8/86 424/70.11 |
| 2005/0142084 A1* | 6/2005 | Ganguly ................. A61K 8/26 424/63 |
| 2006/0065280 A1 | 3/2006 | Cheung ......................... 132/201 |
| 2006/0084586 A1* | 4/2006 | Drzewinski ............ A61K 8/817 510/119 |
| 2007/0077222 A1 | 4/2007 | Shapiro et al. ................. 424/74 |

(Continued)

FOREIGN PATENT DOCUMENTS

| | | | | |
|---|---|---|---|---|
| CN | 101341239 | | * 11/2012 | |
| DE | 4331252 | | 5/1994 | ............... A61K 8/19 |

(Continued)

OTHER PUBLICATIONS

Mayo clinic Caffeine content for coffee, tea, soda and more, brewed, decaf coffee contains 2-2-5 mg of caffeine (https://www.mayoclinic.org/healthy-lifestyle/nutrition-and-healthy-eating/in-depth/caffeine/art-20049372).*

(Continued)

*Primary Examiner* — Danah Al-Awadi
(74) *Attorney, Agent, or Firm* — Ernest D. Buff & Associates, LLC; Ernest D. Buff; Margaret A. LaCroix

(57) ABSTRACT

An improved hair color formulation treats hair to provide volume, viscosity, color and hair follicle stimulation. The color formulation is appointed to be used in hair products, and comprises a natural color agent and at least one agent providing anti-dihydrotestosterone (DHT) effects. Hair products include styling products, cleansing products, concealment products, and dying products. In one embodiment, the formulation comprises an aqueous emulsion, at least one hydrocarbon, at least one thickening agent, at least one humectant, at least one emollient, at least one fatty acid ester, and at least one agent providing anti-dihydrotestosterone (DHT) effects, such as caffeine, and at least one color agent. Preservatives, fibers and further treatments for male/female pattern baldness may also be added to the composition. Natural colorants are added to the hair color formulation to provide temporary coloring in addition to enhanced volume, viscosity and hair follicle stimulation.

3 Claims, No Drawings

(56) References Cited

U.S. PATENT DOCUMENTS

| | | | |
|---|---|---|---|
| 2007/0202064 A1* | 8/2007 | Drzewinski | A61K 8/817 424/70.1 |
| 2007/0272263 A1 | 11/2007 | Gold | 132/201 |
| 2008/0261896 A1 | 10/2008 | Tanaka et al. | 514/25 |
| 2008/0279805 A1 | 11/2008 | Giroud | 424/70.16 |
| 2009/0061004 A1* | 3/2009 | Birkel | A61K 8/025 424/489 |
| 2009/0220445 A1 | 9/2009 | Hessefort et al. | 424/70.2 |
| 2009/0274642 A1 | 11/2009 | Dawson et al. | 424/74 |
| 2010/0043819 A1 | 2/2010 | Feng et al. | 132/217 |
| 2010/0242982 A1 | 9/2010 | Prem et al. | 132/208 |
| 2011/0182826 A1* | 7/2011 | Boyke | A61K 8/35 424/10.3 |
| 2012/0121721 A1* | 5/2012 | James | A61K 8/9789 424/537 |
| 2012/0141406 A1 | 6/2012 | Knappe et al. | 424/70.16 |
| 2012/0157478 A1 | 6/2012 | Dawson et al. | 514/263.34 |
| 2012/0199152 A1 | 8/2012 | Shapiro et al. | 132/202 |
| 2013/0115182 A1 | 5/2013 | Goralczyk | 424/70.6 |
| 2013/0184243 A1* | 7/2013 | Alonso | A61K 45/06 514/171 |
| 2014/0050686 A1 | 2/2014 | Knappe et al. | 424/70.16 |
| 2014/0079686 A1 | 3/2014 | Barman et al. | 424/94.67 |
| 2014/0102467 A1 | 4/2014 | Pistorio et al. | 132/202 |
| 2014/0227363 A1* | 8/2014 | Drapeau | A61K 8/9789 424/535 |
| 2015/0231050 A1* | 8/2015 | Lan | A61K 8/60 8/432 |

FOREIGN PATENT DOCUMENTS

| | | | | |
|---|---|---|---|---|
| DE | 10239473 | | 12/2003 | A41G 5/00 |
| DE | 102005010142 | * | 2/2005 | |
| DE | 102006050984 | * | 4/2008 | |
| DE | 10 2013 01668 | | 10/2013 | A61K 8/97 |
| JP | 2005053816 | * | 3/2005 | |
| KR | 100834891 | * | 6/2008 | |
| KR | 10220090085765 | * | 8/2009 | |
| WO | WO/1989/009046 | | 10/1989 | A61K 8/41 |
| WO | WO 2000067710 | * | 11/2000 | |
| WO | WO 2002017867 | * | 3/2002 | |
| WO | WO 2014029352 | * | 2/2014 | |

OTHER PUBLICATIONS

"How to Sucessfully use a Conditioner as a Styler" 2016.*
Curltalk-Deep Conditioner as styler? 2014.*
https://www.lovethyhns.ca/curl-junkie-coffee-coco-curl-creme/ (published 2013) (Coffee-Coco Curl Crème).*
https://web.archive.org/web/20130314034632/http://www.feingold.org/Research/PDFstudies/colors.pdf entitled "Food Chemistry" by Kiran Naz (Hereafter Naz).*
Kianna https://bglh-marketplace.com/2013/11/chocolate-for-natural-hair-oh-yes-2-cocoa-powder-hair-mask-recipes/ 2013.*
"Hair Cubed" at "Hair Cubed" is found at http://www.haircubed.com/index.php?target=pages&page_id=how_it_works&l=e.
"Hair Loss Concealers" found at http://www.folica.com/hair-loss/hair-loss-concealers?gclid=CJm27deukrsCFc07OgoduhAA8A.
"Nourishing Color Enhancing Hair Mask for Dark Hair at Home" (MarineWife0311) Nov. 7, 2012 (Nov. 7, 2012) [online] retrieved from <URL:httpps://www.youtube.com/watch?v=sU71km2mlaU> entire document, especially demonstration 0:10-2:00.accessed Nov. 19, 2015.
"Coloring grays using cocoa? Is this possible? Will it work?" to Diva_Esq et al. Long Hair Care Forum (hereinafter Esq) Dec. 2011 p. 3, para. 1; p. 3 para 4; p. 5 para.1 https://longhaircareforum.com/threads/coloring-grays-using-cocoa-is-this-possible-will-it-work.586113/.
Anonymous: "Naturbraunes haar intensivieren ohne chemie: Prag Mutti" Retrived form the internet: Aug. 23, 2010 @https://www.frag-muti.de/naturbraunes-haar-intensivieren-ohne-dhemie-a21067/ ; Translation included.

* cited by examiner

VOLUME BOOSTING MOLDING HAIR COLORING CREME FORMULATION

CROSS-REFERENCE TO RELATED APPLICATIONS

The present application claims the benefit of U.S. Provisional Patent Application 61/999,007, entitled "Volume Boosting Molding Hair Crème Formulation", filed on Jul. 14, 2014, and also the benefit of U.S. Provisional Patent Application 61/999,009, entitled "Volume Boosting Molding Hair Coloring Crème Formulation", filed on Jul. 14, 2014, the disclosures of which are hereby incorporated in their entirety by reference thereto.

FIELD OF THE INVENTION

The present disclosure generally relates to hair formulations for styling and altering the appearance, color and/or texture of a user's hair; and more particularly, to a molding crème adapted to mold hair while providing temporary hair color and treatments, conditioning properties, thicker texture and volume.

DESCRIPTION OF RELATED ART

Hair care products represent a large share of the cosmetic market. Products include molding crèmes that are used to hold hair in a given style or orientation, volumizing crèmes and sprays intending to give hair the appearance of increased flow and volume, hair dying crèmes, conditioning crèmes and thickening crèmes. Various hair care products are currently provided to treat male and/or female pattern baldness issues in attempt to reduce or slow down baldness, conceal bald spots, and/or to provide treatment for hair growth.

Examples of various hair care products and treatments are set forth below in summation:

U.S. Pat. No. 3,811,830 to Demarco discloses a hair dye composition in the form of an oil-in-water emulsion, where the dye is dissolved or finely dispersed in said oil phase. The composition contains a coupling agent (e.g., water soluble alkylene glycols or alkylene glycol ether alcohols; long-chain, fatty acid soaps; or long-chain fatty compound polyoxyalkyl or polyhydroxyalkyl derivatives), which imparts stability to the emulsion.

U.S. Pat. No. 4,898,595 to Fridd et al. discloses coloring keratinous material. This system and method discloses a process for coloring hair in which certain linear polysiloxanes including siloxane units having a silicon bonded hydroxy group are employed to provide improved depth of color or color retention. Preferably the polysiloxanes are employed as a treatment on hair prior to or after application of colorant. The application of pyroxene composition prior to applying color allows better bonding of the hair dye to the hair and keeps the color during multiple hair washings.

U.S. Pat. No. 5,112,359 to Murphy et al. discloses a composition of dispersant free substituted diaminoanthaquinone colorants to be used in hair dyes, coloring kits, mousses, gels and aerosols. By use of said diaminoanthraquinones containing compositions, the keratin fibers which make-up hair can be colored to very intense shades.

U.S. Pat. No. 5,436,010 to Lau et al. discloses an HS-GL product that achieves complete penetration as a carrier system to the level of the spiral cell in the functional protofibril, which is capable of migrating to the central medulla region in the cortex of the hair shaft in the morphological model. This penetration of the hair shaft is achieved by the combination of microfluidized hydroxylated lecithin and glycerin, which is unique to this invention because penetration is minimal or incomplete when either hydroxylated lecithin, even though microfluidized to hydroxysphere form, or glycerin are treated separately as individual penetrating agents.

U.S. Pat. No. 5,747,016 to Yui et al. discloses organopolysiloxanes and a method of setting hair using the same. This organopolysiloxane generates intramolecular or intermolecular cross-linking based on dipole-dipole interaction, hydrogen bonding or ion bonding, and which is not ruptured or plastically deformed at an extension ratio no more than 15% at a temperature of 20° C. under relative humidity of 65%; and provides a method of setting hair.

U.S. Pat. No. 6,110,474 to Roman discloses a pigment composition comprising an effective amount of an aqueous extract of coffee and at least one organic pigment. The pigment compositions are useful in preparing cosmetic formulations in which a true black color in the final product is needed. In particular, the pigment composition is useful in the preparation of eyeliner, lash coloring, and hair dyes or rinses.

U.S. Pat. No. 6,132,704 to Bhatt et al. discloses hair styling gels that are applied to the hair in order to shape style, detangle and condition the hair, which are washable from the treated hair. These gels comprise a carboxylated polyurethane resin, an optional second hair fixative resin, a viscosity enhancer, and a carrier comprising Water. The optional second hair fixative resin is a traditional hair setting resin, such as a vinyl or acrylic resin. The optional second hair fixative resin can be an anionic, cationic, or nonionic resin, because each class of resin is compatible with the carboxylated polyurethane resin.

U.S. Pat. No. 6,274,129 to Bhatt et al. discloses hair styling gels that are applied to the hair in order to shape, style, and condition said hair. The hair styling gels containing (i) a hydrophilic, carboxylated polyurethane resin, (ii) an optional second hair fixative resin, (iii) a viscosity enhancer, and (iv) a carrier comprising Water. The optional second hair fixative resin is a traditional hair setting resin, such as a vinyl or acrylic resin. The optional second hair fixative resin can be an anionic, cationic, or nonionic resin because each class of resin is compatible with the carboxylated polyurethane resin.

U.S. Pat. No. 6,627,183 to Young et al. discloses hair-care compositions. The hair care composition comprises: (a) cationic saccharide polymer or copolymer wherein the cationic polymer has a charge density of greater than about 1.5 meq/g, preferably greater than about 1.6 meq/g, more preferably greater than about 1.7 meq/g, even more preferably greater than about 1.8 meq/g; and (b) less than about 5%, preferably less than about 2%, more preferably less than about 1%, even more preferably 0%, by weight, of anionic surfactant. The compositions provide good conditioning/shine to the hair with reduced feelings of tackiness and greasiness.

U.S. Pat. No. 8,002,849 to Prem et al. discloses a composition kit, and method for coloring the hair utilizing saccharide-siloxane copolymers. The method of coloring hair comprises the steps of applying onto the hair a pre-treatment composition containing at least one saccharide-siloxane copolymer to form pre-treated hair, optionally, at least one emulsifier, optionally, at least one viscosity-modifying agent, and a cosmetically acceptable medium; applying a permanent hair coloring composition onto the pre-treated hair to form colored hair, rinsing the colored hair, optionally, applying a post-treatment composition to the hair, and optionally, rinsing the colored hair.

U.S. Pat. No. 8,585,777 to Misu et al. discloses a cosmetic composition for keratin fibers. This cosmetic composition has keratin fibers, and is used for coloring hair or for reshaping hair. The cosmetic composition comprises (a) a phosphoric surfactant; (b) a non-ionic surfactant, (c) a polyol; (d) an oil; and (e) an alkaline agent. It is preferable that the cosmetic composition further comprises at least one higher alcohol. The composition does not generate odor while maintaining a level of cosmetic performance comparable to that of conventional cosmetic compositions.

U.S. Pat. No. 8,585,779 to Sabelle et al. discloses a composition comprising at least one 2-pyrrolidone functionalized in the 4 position with a carboxylic acid or amide, and at least one direct dye or a pigment for dyeing keratin fibers. This composition is for dyeing keratin fibers, and in particular human keratin fibers such as the hair; it comprises at least one 2-pyrrolidone functionalized in the 4 position with a carboxylic acid or amide radical, and at least one hydrophobic direct dye or a pigment. The dyeing process uses this composition. The pyrrolidone component is combined with a direct dye or a pigment for dyeing keratin fibers, and especially to the use of the pyrrolidone component improves the color uptake onto the fibers of direct dyes that are sparingly soluble or insoluble in aqueous-alcoholic supports. The dying process makes it possible to obtain direct dyeing on keratin fibers that is fast, resistant to washing, chromatic and powerful.

U.S. Patent Application Number 2006/0065280 to Cheung discloses a hair extension kit and method of using same. This hair extension kit includes a plurality of hair extensions of novel construction. A method of attaching the hair extensions onto a wearer's natural hair is made possible by using an easy-to-use attachment system. Each of the hair extensions of the hair extension kit includes a malleable or deformable ring, which circumscribes the legs of an extension loop and an elongated strand of supplemental hair. The method of attaching each of the hair extensions to the wearer's natural hair includes the steps of placing the extension loop of each hair extension on top of an existing strand of hair of the wearer; pulling the existing strand of hair through the extension loop so that the strand of hair is disposed inside the extension loop; pulling the extension loop through the malleable or deformable ring in order to draw the extension loop and the strand of supplemental hair through the ring; and securing the strand of supplemental hair and the existing strand of hair within the ring by crimping the malleable or heating the deformable ring.

U.S. Patent Application Number 2007/0272263 to Gold discloses a method for thickening hair, a separator device for receiving hair, an assembly for thickening hair and an applicator for the assembly in the method for thickening hair. A separator device is provided for receiving hair. A method of application of a thickening assembly, comprises first separation tooth elements, being equidistant and arranged such as to subdivide a portion of hair into portions containing basically the same quantity of receiving hair. A bearing surface is provided for arranging in position said adhesive tape delimited on one side by said first tooth elements and second tooth elements arranged on the opposite side with respect to said first tooth elements having with respect to the latter a greater density and interspaces such as to arrest the receiving hair inserted there between. This assembly is appointed for thickening hair with no manual operation required and allows the application of hair extensions in sets, carrying out a perfect integration between the connecting elements supporting the hair extensions and the user's receiving hair.

U.S. Patent Application Number 2008/0279805 to Giroud discloses use of non-film-forming cationic lattices for increasing the volume of hair. This hair treatment composition comprises, a dispersion of non-film-forming cationic latex particles formed from a synthetic polymer, obtained by free-radical polymerization in a cosmetically acceptable liquid medium. The glass transition temperature ($T_g$) of the dispersion particles is greater than or equal to 30° C., with a mean particle size ranging from 10 nm to 200 nm, and with a zeta surface potential (.zeta.) of greater than +20 mV. Such a composition is used for increasing the volume of the hair.

U.S. Patent Application Number 2010/0043819 to Feng et al. discloses compositions containing stimulus sensitive colorant. The compositions containing stimulus sensitive colorant as well as to methods of applying such compositions to keratin materials and kits containing such compositions is described.

U.S. Patent Application Number 2010/0242982 to Prem et al. discloses composition kit, and method for coloring the hair utilizing saccharide-siloxane copolymers. The method of coloring hair, comprising the steps of applying onto the hair a pre-treatment composition containing at least one saccharide-siloxane copolymer to form pre-treated hair, optionally, at least one emulsifier, optionally, at least one viscosity-modifying agent, and a cosmetically acceptable medium; applying a permanent hair coloring composition onto the pre-treated hair to form colored hair, rinsing the colored hair, optionally, applying a post-treatment composition to the hair, and optionally, rinsing the colored hair.

U.S. Patent Application Number 2002/0034485 to Noser et al. discloses a cosmetic composition, especially a hair tonic, for preventing or treating hair loss containing an effective ingredient combination of fatty acids, biotin and/or caffeine. The composition further includes a cosmetic method for increasing natural hair growth and for reduction of hair loss.

U.S. Patent Application Number 2007/0077222 to Shapiro et al. discloses a topical treatment for human hair loss that takes advantage of the natural properties of xanthene derivatives and derivatives of saw palmetto berry and, taken alone or in combination, provides a hair loss product that does not need a prescription for distribution and use. The formulation achieves synergistic results if the saw palmetto berry is an extract applied in a topical preparation and the xanthene, methylxanthene, or caffeine is also applied in the form of a topical preparation.

U.S. Patent Application Number 2012/0141406 to Knappe et al. discloses agents for the treatment of hair, comprising a combination of at least one acrylate-glyceryl acrylate copolymer, at least one film-forming and/or setting polymer, and at least one ester oil. The '406 reference also relates to a method for the cosmetic treatment of keratin-containing fibers.

U.S. Patent Application Number 2012/0199152 to Shapiro et al. discloses compositions for treating hair loss by reducing the effects of 50t-dihydrotestosterone (DHT), which include the following three natural, active ingredients: caffeine, saw palmetto berry extract/derivative, and epigallocatechin-3-gallate (EGCG). Although caffeine, saw palmetto berry and epigallocatechin-3-gallate (EGCG) have been shown to have similar effects, they have never been used together. The invention provides a topical composition for improving treatments for human hair loss (alopecia) by reducing the effects of 50t-dihydrotestosterone (DHT) and thus, enhancing hair loss prevention and/or hair growth promotion.

U.S. Patent Application Number 2014/0050686 to Knappe et al. discloses agents for the treatment of hair, comprising a combination of at least one acrylate-glyceryl acrylate copolymer, at least one film-forming and/or setting polymer, and at least one ester oil. The present invention also relates to a method for the cosmetic treatment of keratin-containing fibers.

U.S. Patent Application Number 2014/0102467 to Pistorio et al. discloses aqueous dispersion comprising: (i) at least one solid wax particle having a particle size ranging from equal to or greater than 1 micron to about 100 microns and comprising at least one wax having a melting point of greater than 35° C.; (ii) a surfactant mixture comprising at least one nonionic surfactant and at least one ionic surfactant; and (iii) water. The aqueous dispersion may be employed in compositions capable of altering the color of various substrates, for example, keratinous substrates such as skin and hair.

Foreign Patent Application Number DE10239473 to Kesler discloses hair replacement method using artificial hair obtained by spraying scalp with plastic particles drawn out into fine filaments. The hair replacement method has the bald areas of the scalp sprayed with plastic particles which are drawn out into fine filaments for acting as artificial hair before hardening, e.g. by combing. The appearance of the artificial hair remains stable for at least a day and is resistant to humidity and rain, the plastic particles sprayed onto the scalp using a spray pump or an aerosol can, with washing for removal of the artificial hair using a solvent solution. An Independent claim for a device for hair replacement is also included.

Foreign. Patent Application Number DE4331252 to Warschkow et al. discloses hair loss treatment and hair regrowth promoter. The hair loss treatment comprises (A) a drink for internal consumption comprising (a) 40-85% diet juice e.g. of tomato, orange, carrot, cherry or grape, (b) 5-35% spray dried L-aminoacids derived from tissue protein, K, Ca, Mg, and fe and (c) 5-55% cold pressed juice of merismatic tissue of tropical green leaf plants such as cactus types and pampas grass, and (B) hair gel for external application comprising (a) 50-95% cold pressed juice of merismatic tissue of tropical green leaf plants such as cactus types and pampas grass treated with gelatinin (sic) stabilisers and (b) 5-30% cold pressed juice of merismatic tissue of green weed plants such as ribwort (*plantago lanceolata*), dandelion (*Taraxacum officinale*) or nettle, with addn. of 30-50% alcohol. The treatment is useful for treating conditions such as male pattern baldness and alopecia areata. The treatment gives immediate reduction in the rate of hair loss to the normal level of 40-120 hairs/day and promotes regrowth of hair in areas where hair loss has taken place.

Foreign. Patent Application Number WO/1989/009046 to Furui discloses topical application of mexiletine in the form of solutions/lotions, gels, ointments, creams or pastes in order to treat baldness or diminished hair growth.

Internet Publication "Hair Cubed" at "Hair Cubed" is found at http://www.haircubed.com/index.php?target=pages&page_id=how_it_works&l=e discloses a hair spray product that covers bald areas generally requiring an additional sealer to hold the coating.

Internet Publication "Hair Loss Concealers" found at http://www.folica.com/hair-loss/hair-loss-concealers?gclid=CJm27deukrsCFc07OgoduhAA8A discloses hair loss concealers that instantly eliminates the appearance of baldness and thinning hair for both men and women through use of keratin fibers.

Despite the presence of heretofore disclosed and/utilized hair care products, certain drawbacks exist. For example, many of the products fail to provide a combination of hair functions—such as styling and molding—while also providing conditioning and nutrients to the hair. As a result, the user must utilize a combination of more than one/several different products in order to achieve the array of objectives sought. Additionally, several of the products adapted to treat baldness have adverse health effects, which over time can cause physical and/or cognitive damage to the user. Damaging side effects have been found to include diminished libido, erectile dysfunction and male breast cancer, depression, brain fog and memory loss, for example.

Accordingly, there exists a need for a hair color formulation adapted to be added to hair products such as hair paste/crème for men and/or women that provides treatment to the hair while enhanced the appearance of hair volume, viscosity and hair vitality through conditioning agents and follicle stimulation. Further, there exists a need for a hair color formulation that molds hair and treats hair with volume boosting properties as well as temporarily color treating hair. Additionally, there exists a need for a hair color formulation that molds hair, volumizes and thickens hair, temporary color treats hair, and provides hair follicle stimulation lessening the effects of dihydrotestosterone in balding.

SUMMARY OF THE INVENTION

The present invention is directed to improved hair color formulations for enhancing hair color and viscosity. Paste compositions for men and/or women are rendered for treating hair to provide enhanced hair volume, viscosity, temporary color and hair follicle stimulation. In a preferred embodiment, the subject improved hair color formulation comprises a natural color agent and at least one agent providing anti-dihydrotestosterone (DHT) effects, the hair color formulation being adapted to be added to hair products. The hair color formulation of preferably is in an aqueous solution or emulsion that is adapted to be added to the hair products. Alternatively, the hair color formulation is a fine powdered mixture adapted to be added to the hair products. Hair products contemplated include a vast array of hair styling products, such as gels, crèmes, sprays, mousses, and pomades. Other hair products contemplated include hair cleansing products such as, shampoos, conditioners, exfoliating scrubs, leave in conditioners, dry shampoos and other cleansing products. Hair concealment products can also be utilized by adding the subject hair color formulation. These products includes dry shampoos, hair building fibers, concealment sprays, mousses, pomades, and other products used to provide a source of nutrition, concealment of minor balding and thinning, natural color and natural ingredients to combat DHT.

In a first broad embodiment, a hair color formulation comprises a natural color agent and at least one agent providing anti-dihydrotestosterone (DHT) effects, the hair color formulation being adapted to be added to hair products. Natural ingredients used in the subject hair color formulation includes, coffee, instant coffee, dark cocoa, charcoal powder, caramel color, and caramel color powder.

The subject hair color formulation can be added to hair styling products such as gels, crèmes, sprays, mousses, pomades, and other styling products and be used for the purposes of providing a source of nutrition, natural color and natural ingredients to combat DHT. The hair color formulation provides immediate coverage of grey hairs. When used every day, the hair color formulation is believed to stain hair follicles. The hair color formulation preferably contains natural caffeine, which may help to reduce the negative (balding) effects of DHT. In a hair spray, the hair color formulation will provide instant natural color and coverage of grey hairs. When used every day, the hair color formulation's color agent may stain hair follicles. Some of these ingredients contain natural caffeine, which may help to reduce the negative (balding) effects of DHT.

Alternatively, the hair color formulation can be added to hair cleansing products such as shampoos, conditioners, exfoliating scrubs, leave in conditioners, dry shampoos and other cleansing products. The hair color formulation can be added to hair cleansing products and provide a source of nutrition, natural color and natural ingredients to combat DHT. When the hair color formulation is used in a hair-cleansing product it will provide nutrition, color, and (with continued use) coverage of grey hairs. When used every day, these ingredients may stain hair follicles. Preferably, the hair color formulation contains natural caffeine, which may help to reduce the negative (balding) effects of DHT. In hair cleansing products, these ingredients added together with a penetrating ingredient may provide immediate staining of hair follicles. The hair color formulation's use of coffee, for example, may be used in raw form to provide a natural exfoliate as well as natural color, and a natural source of caffeine.

In an alternative embodiment, the hair color formulation is appointed to be added to hair concealment products such as dry shampoos, hair building fibers, concealment sprays, mousses, pomades, and others and be used for the purposes of providing a source of nutrition, concealment of minor balding and thinning, natural color and natural ingredients to combat DHT. When the hair color formulation is used in hair concealment product it is adapted to provide immediate coverage of grey hairs. In addition, the hair color formulation's addition to concealment products is appointed to provide instant concealment of minor balding and thinning areas in the scalp. When used every day, the hair color formulation is believed to stain hair follicles and reduce the negative (balding) side effects of DHT through use of the anti-DHT agent, preferably caffeine. In hair concealment products, the hair color formulation can be applied in a wet or dry form. In a dry form, it can be added to concealment hair building fibers. In a wet form, it can be added to sprays, dry shampoo and root coverage applications to provide concealment.

The hair color formulation may be utilized in hair dying products together with a penetrating ingredient as a permanent dye for men and women. It can be added to hair dying products and provide a source of nutrition, natural color and natural ingredients to combat DHT. When the hair color formulation is used in hair-dying products together with a penetrating ingredient, it is adapted to provide nutrition, color, and immediate coverage of grey hairs. Depending on the strength of the penetrating ingredient, the addition of the hair color formulation may provide a natural permanent dye solution. Natural caffeine may be used in the hair color formulation, which may help to reduce the negative (balding) effects of DHT. In hair dying products, the hair color formulation together with a penetrating ingredient may provide immediate staining of hair follicles.

The hair formulation may be used in a hair paste that treats hair with volume boosting molding properties as well as providing a temporary color treatment for the hair. The subject hair formulation and method of use provides an improved color formulation that has a relatively thick viscosity yielding a hair paste that creates a thickening component for increased hair molding and holding capability. Additionally, the improved composition moisturizes hair while increasing elasticity and softness. Temporary coloring agents are included in the composition, including coloring agents ranging from white, red, blonde, light brown, medium brown, dark brown and black hair colors. Preferably, the color agents range from black, dark brown to light brown. Color agents are optimized to prevent color fall out/run off. Color agents utilized are natural ingredients, including coffee, instant coffee, dark cocoa, charcoal powder, caramel color, and caramel color powder, utilized in 1) hair styling products, 2) hair cleansing products, 3) hair concealment products, and 4) hair dying products.

The subject formulation provides a hair paste particularly geared toward men (use by women is contemplated) that provides volume boosting molding properties, as well as temporary color treatment for the hair. The subject system and method provides a product that has a relatively thick viscosity yielding a hair paste that creates a thickening component for increased hair molding and holding capability. Additionally, the composition moisturizes hair while increasing elasticity and softness. Temporary coloring agents are included in the composition, including coloring agents ranging from white, red, blonde, light brown, medium brown, dark brown and black hair colors. Preferably, the color agents are in black, light brown or dark brown color families. Color agents are optimized to prevent color fall out/run off. The composition may further include a fiber component, such as a keratin fiber, that temporarily binds to existing hair and or the scalp to mask thinning areas of the user's hair. Once applied to the hair the paste does not rub off onto materials and stays on the hair until it is washed out with shampoo. When applied to the hair, the subject composition hides gray hair, roots, adds volume, adds color, and covers thinning or bald spots.

The composition includes an anti Dihydrotestosterone (5α-Dihydrotestosterone) (DHT) agent in an aqueous emulsion containing at least one hydrocarbon, thickening agents, humectants, emollients, and fatty acid ester. DHT is a male sex hormone believed to influence hair loss and balding. 5α-reductase, an enzyme, has been found to synthesize DHT in the adrenal glands, hair follicles, testes and prostate. As a consequence of changes in the metabolism of androgen in the body, it has been found that male and female adults are subject to hair loss, effecting men more commonly than women. It is believed that DHT plays a major role in hair loss. 5α-reductase inhibitors are commonly used for the treatment of male pattern baldness in inhibiting DHT-producing enzyme. However, 5α-reductase inhibitors are thought to have damaging side effects that can persist after stopping the treatment, such as diminished libido, erectile dysfunction and male breast cancer, depression, brain fog and memory loss.

The subject composition provides a volume boosting molding crème that contemporaneously treats balding by stimulating follicles to grow and yielding an anti DHT agent effect treatment to the scalp. Delivery of the anti DHT agent and treatment of balding are effective owing to the nourishing composition and follicle stimulating properties of the subject crème. Additionally, volume boosting properties of the subject crème provide for an increased visible appearance of hair while treating baldness. When applied to the hair, the subject composition adds volume along the hair shaft extending from the roots, adds color and hides grey hair, all while treating thinning or bald spots.

In one embodiment, an improved hair color formulation is provided for providing enhanced hair volume, viscosity, color and hair follicle stimulation. The hair color formulation adapted for treating hair to provide enhanced hair volume, viscosity and hair follicle stimulation comprises an aqueous emulsion, at least one hydrocarbon, at least one thickening agent, at least one humectants, at least one emollient, at least one fatty acid ester, and at least one agent providing anti-dihydrotestosterone (DHT) effects, the improvement comprising at least one color agent comprising dark cocoa and instant coffee to provide hair color treatment adapted to enhance hair appearance. Preservatives, fibers (such as keratin fiber or powder held in suspension by use of surfactants and thickeners) and further treatments for male/female pattern baldness may also be added to the composition. Natural colorants are added to the hair color formulation to provide temporary coloring in addition to enhanced volume, viscosity and hair follicle stimulation.

In another embodiment a hair color formulation is provided that is adapted for treating hair to provide enhanced hair volume, viscosity and hair follicle stimulation comprising an aqueous emulsion containing water ranging from 32-72 wt %, at least one hydrocarbon ranging from 4-13 wt %, at least one thickening agent ranging from 2-14% wt. %, at least one humectant ranging from 2.5-13 wt %, at least one emollient ranging from 3.1-20.3 wt %, at least one fatty acid ester ranging from 5-12 wt. %, and at least one agent providing anti-dihydrotestosterone (DHT) effects, said anti DHT agent ranging from 0.01-0.8 wt. %, the improvement comprising at least one color agent comprising dark cocoa and instant coffee to provide hair color treatment adapted to enhance hair appearance.

Hydrocarbons preferably includes petroleum compounds. Thickening agents preferably include cetyl alcohol, Sodium Polyacrylate Sunflower Seed Wax for examples; humectants may be for example a glycerol, glycerin, disodium EDTA, Sorbito, etc.; emollients are preferably a combination of waxes. Waxes contemplated include carnuba wax, cetyl esters wax, emulsifying wax, methylparaben, and ethylparaben. In addition to the composition, fibers, keratin fibers, and/or oat fiber may be used in the composition. Emollients may further include at least one fatty acid ester. Fatty acids include, but are not limited to simple esters with lower chain alcohols (methyl-, ethyl-, n-propyl-, isopropyl- and butyl esters). Preservatives, further colorants (temporary and/or permanent) and male pattern baldness treatments may be added to the composition.

In another embodiment, a hair color formulation comprising an aqueous emulsion, at least one agent providing anti-dihydrotestosterone (DHT) effects is provided. The hair color formulation being adapted to either be used alone as a clear application or to be added to hair products.

A hair color formulation is also provided comprising an aqueous emulsion, at least one agent providing anti-dihydrotestosterone (D.H.T.) effects and at least one of each of the following: i) agent adapted to provide anti-dihydrotestosterone (D.H.T.) effects; ii) sequestrant; iii) essential ingredients (Egel); iv) carbomer; v) styling glue; vi) emulsion stabilizer; and vii) silicone, said hair base formulation being adapted to either be used alone as a clear application or to be added to hair products. The hair color formulation as may further comprise an Acrylates Copolymer, such as that sold under the trade name Carbopol® Aqua SF-1 Polymer sold by Lubrizol. Carbopol® Aqua SF-1 polymer is a lightly cross-linked acrylate copolymer. It is a novel, liquid, acrylic rheology modifier designed to suspend, stabilize, thicken, and enhance the appearance of surfactant-based personal cleansing products and soap-based cleansing systems. Preferably, the Acrylates Copolymer ranges from 0.3-3.0 wt. %. Preferably, the sequestrant is Disodium EDTA. The Egel ranges from 0.2-4.5 wt. %; more preferably the Egel ranges from 0.20-0.75 wt. %; most preferably the Egel is 0.46 wt. %.

The carbomer is preferably a cross-linked polyacrylic acid polymer that provides efficient rheology modification with enhanced self-wetting for case of use, such as that sold under the trade name Carbopol® Ultrez 10 Polymer. Preferably, the carbomer ranges from 0.2-3.0 wt. %; more preferably the carbomer ranges from 0.20-0.75 wt. %; most preferably the carbomer is 0.45 wt. %.

The styling glue is preferably comprised of Di Water, Disodium EDTA, Glycerin, Polyethylene, Polyvinylpyrrolldone, Sodium Polyacyrlate, Octyl Palmitate, Hydrolyzed Soy Protein, Propylene Glycol, Dlazoildinyl Urea, Methyl Paraben, Propyl Paraben—such as that sold under the trade name Jeesperse CPW-2 PVPK-30 Styling Glue J21-63KZ sold by Jeen. The styling glue preferably ranges from 0.20-0.75 wt. % most preferably the styling glue is 0.44 wt. %.

As indicated, the hair color formulation may further contain the addition of colorants, and more preferably natural colorants, thereby providing a hair paste that provides volume boosting molding properties as well as temporary color treatment for the hair. Temporary coloring agents are preferably included in the composition, including coloring agents ranging from white, red, blonde, light brown, medium brown, dark brown and black hair colors. Preferably, the color agents are in black, light brown or dark brown. Color agents are optimized to prevent color fall out/run off.

The hair color formulation preferably includes at least one preservative. The preservative is preferably selected from Phenoxethanol, Caprylyl Glycol, Potassium Sorbate, Laurtrimonium Chloride, and Triethanolamine. The hair color formulation anti DHT agent preferably comprises caffeine.

The improved hair color formulation includes at least one coloring agent. In one embodiment the hair color formulation further comprises charcoal powder ranging from 0.3-2 wt. %, dark cocoa ranging from 0.001-0.5 wt. %, and instant coffee ranging from 0.001-0.5 wt. %, yielding a black hair color formulation. In another embodiment the hair color formulation further comprises caramel color ranging from 0.02-3 wt. %, caramel color powder ranging from 0.02-3 wt. %, dark cocoa ranging from 0.001-0.5 wt. %, instant coffee ranging from 0.001-0.5 wt. %, and charcoal powder ranging from 0.005-0.5 wt. %%, yielding a brown hair color formulation. In another embodiment the hair color formulation further comprises caramel color ranging from 0.02-3 wt. %, caramel color powder ranging from 0.02-3 wt. %, dark cocoa ranging from 0.001-0.5 wt. %, and instant coffee ranging from 0.001-0.5 wt. %, yielding a light brown hair color formulation.

DETAILED DESCRIPTION OF THE DISCLOSURE

The best mode for carrying out the present disclosure is presented in terms of the embodiments herein. The embodiment(s) described herein detail for illustrative purposes and is subject to many variations. It is understood that various omissions and substitutions of equivalents are contemplated as circumstances may suggest or render expedient, but are intended to cover the application or implementation without departing from the spirit or scope of the present disclosure. Further, it is to be understood that the phraseology and terminology employed herein are for the purpose of the description and should not be regarded as limiting. Any of the headings utilized within description are for convenience only and have no legal or limiting effect.

Growing environmental concerns have led to changes in the production process and in the packaging of industry products in the past few years. Products and their packaging are increasingly designed to minimize waste and environmental alterations. Recycled paper is now used to box many cosmetics, while many shampoos and lotions come in post-consumer plastic containers. Consumers are also increasingly interested in cosmetic and beauty products that are themselves organic, healthy and environmentally friendly. Increased concerns about carbon footprints will also encourage manufacturers to find new eco-friendly resources, develop new products and introduce new packaging. Likewise, consumers' need for products made with fewer ingredients, as well as natural ingredients, continue to shape demand for organic, more natural goods.

Research has linked certain cosmetics ingredients to long-term health problems like cancer, which has caused many consumers to shy away from traditional makeup. As such, products featuring natural and organic components are increasingly gaining favor on the market. Similarly, consumers concerned with the negative environmental effects of personal care item production and disposal are increasingly opting for "green" items. Environmental concerns can range from company hiring practices to the plant species used in certain products.

The subject hair formulations provides an environmentally friendly, natural product that provides solutions to a plethora of hair care concerns in a single product, so that users do not have to purchase different products to address hair concerns. Specifically, the subject hair formulation provides a source of nutrition, color, volume, concealment and function. Hair concerns addressed by the subject hair formulation include, volume and moisture, 100% natural color, and follicle stimulating ingredients. In another embodiment, the subject hair formulation functions to provide style and moisture, volume, 100% natural color and stimulation of follicle growth.

The subject improved hair color formulation is volume boosting grooming crème that is a pliable styler that adds volume, body, color and nutrients simultaneously. The formulation includes thickening ingredients that add volume and body to hair; hydrating ingredients that add moisture and softness to dry/hard hair; and color ingredients that add color to gray hair and provide natural nutrients that adds shine to dull hair and/or body to thin hair. Benefits and advantageous of the subject improved hair color formulation are multifunctional, providing: 100% natural color; cover grays within seconds; natural source of caffeine; heat activated volume-boosting technology; follicle hydration technology; covers gray hairs, adds volume, softness and shine simultaneously.

The subject hair formulation revolutionizes hair styling products by providing a single product with multifaceted functions, all in one product. Users will not have to purchase or utilize multiple products to cover gray hair, add volume, and style hair, saving time and money. The formulation uses 100% natural colorants so that the hair styling product does more than just style.

Advantageous of using the subject hair formulation includes: avoiding anxiety/embarrassment with trips to the salon; replacing time consuming at home dye kits; easier/faster application: respectable, affordable, practical method to color grays and style hair within seconds, adds softness, body, shine, volume and color to roots within seconds; replaces touch-up brushes/pens and dry shampoos; matches almost all shades from black to blonde.

In a preferred embodiment, the subject improved hair color formulation comprises a natural color agent and at least one agent providing anti-dihydrotestosterone (DHT) effects, the hair color formulation being adapted to be added to hair products. The hair color formulation of preferably is in an aqueous solution or emulsion that is adapted to be added to the hair products. Alternatively, the hair color formulation is a fine powdered mixture adapted to be added to the hair products. Hair products contemplated include a vast array of hair styling products, such as gels, crèmes, sprays, mousses, and pomades. Other hair products contemplated include hair cleansing products such as, shampoos, conditioners, exfoliating scrubs, leave in conditioners, dry shampoos and other cleansing products. Hair concealment products can also be utilized by adding the subject hair color formulation. These products includes dry shampoos, hair building fibers, concealment sprays, mousses, pomades, and other products used to provide a source of nutrition, concealment of minor balding and thinning, natural color and natural ingredients to combat DHT.

The hair color formulation can be added to hair styling products such as gels, crèmes, sprays, mousses, pomades, and other styling products and be used for the purposes of providing a source of nutrition, natural color and natural ingredients to combat DHT. The hair color formulation provides immediate coverage of grey hairs. When used every day, the hair color formulation is believed to stain hair follicles. The hair color formulation preferably contains natural caffeine, which may help to reduce the negative (balding) effects of DHT. In a hair spray, the hair color formulation will provide instant natural color and coverage of grey hairs. When used every day, the hair color formulation's color agent may stain hair follicles. Some of these ingredients contain natural caffeine, which may help to reduce the negative (balding) effects of DHT.

Alternatively, the hair color formulation can be added to hair cleansing products such as shampoos, conditioners, exfoliating scrubs, leave in conditioners, dry shampoos and other cleansing products. The hair color formulation can be added to hair cleansing products and provide a source of nutrition, natural color and natural ingredients to combat DHT. When the hair color formulation is used in a hair-cleansing product it will provide nutrition, color, and (with continued use) coverage of grey hairs. When used every day, these ingredients may stain hair follicles. Preferably, the hair color formulation contains natural caffeine, which may help to reduce the negative (balding) effects of DHT. In hair cleansing products, these ingredients added together with a penetrating ingredient may provide immediate staining of hair follicles. The hair color formulation's use of coffee, for example, may be used in raw form to provide a natural exfoliate as well as natural color, and a natural source of caffeine.

In an alternative embodiment, the hair color formulation is appointed to be added to hair concealment products such as dry shampoos, hair building fibers, concealment sprays, mousses, pomades, and others and be used for the purposes of providing a source of nutrition, concealment of minor balding and thinning, natural color and natural ingredients to combat DHT. When the hair color formulation is used in hair concealment product it is adapted to provide immediate coverage of grey hairs. In addition, the hair color formulation's addition to concealment products is appointed to provide instant concealment of minor balding and thinning areas in the scalp. When used every day, the hair color formulation is believed to stain hair follicles and reduce the negative (balding) side effects of DHT through use of the anti-DHT agent, preferably caffeine. In hair concealment products, the hair color formulation can be applied in a wet or dry form. In a dry form, it can be added to concealment hair building fibers. In a wet form, it can be added to sprays, dry shampoo and root coverage applications to provide concealment.

The hair color formulation may be utilized in hair dying products together with a penetrating ingredient as a permanent dye for men and women. It can be added to hair dying products and provide a source of nutrition, natural color and natural ingredients to combat DHT. When the hair color formulation is used in hair-dying products together with a penetrating ingredient, it is adapted to provide nutrition, color, and immediate coverage of grey hairs. Depending on the strength of the penetrating ingredient, the addition of the hair color formulation may provide a natural permanent dye solution. Natural caffeine may be used in the hair color formulation, which may help to reduce the negative (balding) effects of DHT. In hair dying products, the hair color formulation together with a penetrating ingredient may provide immediate staining of hair follicles.

The hair formulation may be used in a hair paste that treats hair with volume boosting molding properties as well as providing a temporary color treatment for the hair. The subject hair formulation and method of use provides an improved color formulation that has a relatively thick viscosity yielding a hair paste that creates a thickening component for increased hair molding and holding capability. Additionally, the improved composition moisturizes hair while increasing elasticity and softness. Temporary coloring agents are included in the composition, including coloring agents ranging from white, red, blonde, light brown, medium brown, dark brown and black hair colors. Preferably, the color agents range from black, dark brown to light brown. Color agents are optimized to prevent color fall out/run off. Color agents utilized are natural ingredients, including coffee, instant coffee, dark cocoa, charcoal powder, caramel color, and caramel color powder, utilized in 1) hair styling products, 2) hair cleansing products, 3) hair concealment products, and 4) hair dying products.

The subject formulations provide an improved hair color formulation adapted for treating hair to provide enhanced hair volume, viscosity, color and hair follicle stimulation. A new color formulation for enhancing hair color and viscosity is provided. The colors are derived from addition of coffee, cocoa or charcoal. The hair color formulation comprises an aqueous emulsion containing at least one hydrocarbon, at least one thickening agent, at least one humectant, at least one emollient, at least one fatty acid ester, and at least one agent providing anti-dihydrotestosterone (DHT) effects. Preservatives, additional colorants, fibers (such as keratin fiber or powder held in suspension by use of surfactants and thickeners) and further treatments for male/female pattern baldness may also be added to the composition. Natural colorants such as charcoal powder, caramel color powder, dark cocoa, and/or instant coffee may be added to the hair color formulation to provide temporary coloring in addition to enhanced volume, viscosity and hair follicle stimulation.

A three prong approach to volumization of the hair that works in cold and heat applications (blow dry) is implemented by the subject hair color formulation. This unique approach is to use humectant sugar alcohols, glycerin and sorbitol which have the ability for water retention hold within the hair shaft, along with waxes when dry causing a water retaining volumized appearance. This gel is also different from the boost gel in that it contains wheat protein that acts as nutrients for the hair follicle. This gel is also different from the boost gel in that it contains "caffeine" which has been shown in studies to "stimulate hair follicle growth" as well as suppress the negative effects of DHT which is the main cause of Androgenic Alopecia/Hereditary Hair Loss.

Androgenic Alopecia (AGA) is a common problem in men of all ages, commonly beginning at 20 years of age with a prevalence of approximately 50% by the age of 50. Testosterone is a derivative of DHT. It has been found that the conversion of both agents result in the shortening of hair growth, causing AGA. Effect of caffeine and testosterone on the proliferation of human hair follicles in vitro can be found at http://www.ncbi.nlm.nih.gov/pubmed/17214716. Caffeine and testosterone have been found to have effects on human hair follicles. Significant growth suppression have been found in hair follicles treated with testosterone (Derivative of DHT). It has been found that the higher concentration of testosterone used aggressively suppresses hair follicle growth. It has been found that caffeine counteracts the effects that testosterone has on the hair follicles. Caffeine has been found to not only counteract the effects of testosterone but has been found to lead to a significant stimulation of hair follicle growth as well. In conclusion, it has been found that caffeine alone may act as a powerful stimulator of human hair growth. Accordingly, without being limited by theory, it has been found that caffeine can play a very important role in the clinical impact of the management of AGA. For articles addressing the issue in detail also see: http://www.ncbi.nlm.nih.gov/pubmed/22171682; http://www.ncbi.nlm.nih.gov/pubmed/19694736; http://www.ncbi.nlm.nih.gov/pubmed/18070215.

The composition includes an anti Dihydrotestosterone (5α-Dihydrotestosterone) (DHT) agent in an aqueous emulsion containing at least one hydrocarbon, thickening agents, humectants, emollients, and fatty acid ester. DHT is a male sex hormone believed to influence hair loss and balding. 5α-reductase, an enzyme, has been found to synthesize DHT in the adrenal glands, hair follicles, testes and prostate. As a consequence of changes in the metabolism of androgen in the body, it has been found that male and female adults are subject to hair loss, effecting men more commonly than women. It is believed that DHT plays a major role in hair loss. 5α-reductase inhibitors are commonly used for the treatment of male pattern baldness in inhibiting DHT-producing enzyme. However, 5α-reductase inhibitors are thought to have damaging side effects that can persist after stopping the treatment, such as diminished libido, erectile dysfunction and male breast cancer, depression, brain fog and memory loss.

The subject hair color formulation utilizes a novel combination of agents delivered within an aqueous emulsion. In combination, the subject hair color formulation includes at least one hydrocarbon, at least one thickening agent, at least one humectant, at least one emollient, at least one fatty acid ester, and at least one agent providing anti-dihydrotestosterone (DHT) effects. Synergy within the formulation yields a hair product that not only molds hair, but provides volumizing effects causing hair strands to appear thicker and provides conditioning nutrient delivery to the hair shaft and follicle. Anti DHT agent effects are yielded through use of all natural, safe, healthy components, allowing the subject hair color to be utilized daily without any adverse reactions. In a preferred embodiment, caffeine is utilized as the anti DHT agent causing effects as the caffeine is believed, without being bound by said theory, to stimulate the hair follicles. Delivery of the anti DHT agent and treatment of balding are effective owing to the nourishing composition and follicle stimulating properties of the subject crème. Anti DHT agent effects are provided without the adverse physical and cognitive reactions found in enzyme inhibiting topical treatments.

Through use of the subject hair paste for men and/or women molding and sculpting of the hair is provided treating hair to enhance hair volume, viscosity and hair follicle stimulation. Optionally, the subject hair formulation provides a hair paste that treats hair with volume boosting molding properties as well as temporary color treatment for the hair. The subject hair formulation and method of use thereof provides a molding crème that has a relatively thick viscosity yielding a hair paste that creates a thickening component for increased hair molding and holding capability. Additionally, the composition moisturizes hair while increasing elasticity and softness. Temporary coloring agents are preferably included in the composition, including coloring agents ranging from white, red, blonde, light brown, medium brown, dark brown and black hair colors. Preferably, the color agents are in black, light brown or dark brown. Color agents are optimized to prevent color fall out/run off.

In a first embodiment, the subject hair color formulation provides a formulation adapted for enhancing hair volume and viscosity comprising, in combination, the following salient features: (i) an aqueous emulsion containing at least one hydrocarbon, (ii) at least one thickening agent, (iii) at least one humectant, (iv) at least one emollient, (v) at least one fatty acid ester, and (vi) at least one agent providing anti-dihydrotestosterone (DHT) effects. Each of these elements provides different functions to the formulation. Preservatives, colorants, fibers (such as keratin fiber or powder held in suspension by use of surfactants and thickeners) and further treatments for male pattern baldness are also added to the composition.

In another embodiment a hair color formulation adapted for treating hair to provide enhanced hair volume and viscosity is provided, comprising: an aqueous emulsion containing water ranging from 32-72 wt %; at least one hydrocarbon ranging from 4-13 wt %; at least one thickening agent ranging from 2-14% wt. %; at least one humectant ranging from 2.5-13 wt %; at least one emollient ranging from 3.1-20.3 wt %; at least one fatty acid ester ranging from 5-12 wt. %; and at least one anti DHT agent ranging from 0.01-0.8 wt. %.

Hydrocarbons preferably includes petroleum compounds. Thickening agents preferably include cetyl alcohol, Sodium Polyacrylate Sunflower Seed Wax for examples; humectants may be for example a glycerol, glycerin, disodium EDTA, Sorbito, etc.; emollients are preferably a combination of waxes. Waxes contemplated include carnuba wax, cetyl esters wax, emulsifying wax, methylparaben, and ethylparaben. In addition to the composition, fibers, keratin fibers, and/or oat fiber may be used in the composition. Emollients may further include at least one fatty acid ester. Fatty acids include, but are not limited to simple esters with lower chain alcohols (methyl-, ethyl-, n-propyl-, isopropyl- and butyl esters). Preservatives, further colorants and male pattern baldness treatments may be added to the composition.

In another embodiment, a hair color formulation comprising an aqueous emulsion, at least one agent providing anti-dihydrotestosterone (DHT) effects is provided. The hair color formulation being adapted to either be used alone as a clear application or to be added to hair products.

A hair color formulation is also provided comprising an aqueous emulsion, at least one agent providing anti-dihydrotestosterone (D.H.T.) effects and at least one of each of the following: i) agent adapted to provide anti-dihydrotestosterone (D.H.T.) effects; ii) sequestrant; iii) essential ingredients (Egel); iv) carbomer; v) styling glue; vi) emulsion stabilizer; and vii) silicone, said hair base formulation being adapted to either be used alone as a clear application or to be added to hair products. The hair color formulation as may further comprise an Acrylates Copolymer, such as that sold under the trade name Carbopol® Aqua SF-1 Polymer sold by Lubrizol. Carbopol® Aqua SF-1 polymer is a lightly cross-linked acrylate copolymer. It is a novel, liquid, acrylic rheology modifier designed to suspend, stabilize, thicken, and enhance the appearance of surfactant-based personal cleansing products and soap-based cleansing systems. Preferably, the Acrylates Copolymer ranges from 0.3-3.0 wt. %. Preferably, the sequestrant is Disodium EDTA. The Egel ranges from 0.2-4.5 wt. %; more preferably the Egel ranges from 0.20-0.75 wt. %; most preferably the Egel is 0.46 wt. %.

The carbomer is preferably a cross-linked polyacrylic acid polymer that provides efficient rheology modification with enhanced self-wetting for ease of use, such as that sold under the trade name Carbopol® Ultrez 10 Polymer. Preferably, the carbomer ranges from 0.2-3.0 wt. %; more preferably the carbomer ranges from 0.20-0.75 wt. %; most preferably the carbomer is 0.45 wt. %.

The styling glue is preferably comprised of Di Water, Disodium EDTA, Glycerin, Polyethylene, Polyvinylpyrrolldone, Sodium Polyacrylate, Octyl Palmitate, Hydrolyzed Soy Protein, Propylene Glycol, Dlazoildinyl Urea, Methyl Paraben, Propyl Paraben—such as that sold under the trade name Jeesperse CPW-2 PVPK-30 Styling Glue J21-63KZ sold by Jeen. The styling glue preferably ranges from 0.20-0.75 wt. % most preferably the styling glue is 0.44 wt. %.

As indicated, the improved hair color formulation may further contains the addition of colorants, and more preferably natural colorants, thereby providing a hair paste that provides volume boosting molding properties as well as temporary color treatment for the hair. Temporary coloring agents are preferably included in the composition, including coloring agents ranging from white, red, blonde, light brown, medium brown, dark brown and black hair colors. Preferably, the color agents are in clear (or lack of color), black, light brown or dark brown. Color agents are optimized to prevent color fall out/run off.

The hair color formulation preferably includes at least one preservative. The preservative is preferably selected from Phenoxethanol, Caprylyl Glycol, Potassium Sorbate, Laurtrimonium Chloride, and Triethanolamine. The hair color formulation anti DHT agent preferably comprises caffeine.

The improved hair color formulation includes at least one coloring agent. In one embodiment the hair color formulation further comprises charcoal powder ranging from 0.3-2 wt. %, dark cocoa ranging from 0.001-0.5 wt. %, and instant coffee ranging from 0.001-0.5 wt. %, yielding a black hair volumizing color crème. In another embodiment the hair color formulation further comprises caramel color ranging from 0.02-3 wt. %, caramel color powder ranging from 0.02-3 wt. %, dark cocoa ranging from 0.001-0.5 wt. %, instant coffee ranging from 0.001-0.5 wt. %, and charcoal powder ranging from 0.005-0.5 wt. %, yielding a brown hair volumizing color crème. In another embodiment the hair color formulation further comprises caramel color ranging from 0.02-3 wt. %, caramel color powder ranging from 0.02-3 wt. %, dark cocoa ranging from 0.001-0.5 wt. %, and instant coffee ranging from 0.001-0.5 wt. %, yielding a light brown hair volumizing color crime.

Table I below sets forth an embodiment of the hair color formulation, setting forth a plurality of blending materials and the preferred weight percent ranges utilized to yield a clear hair color crème being volume boosting moulding crème formulation wherein at least one coloring agent is added to yield an improved hair color formulation (Tables below illustrate improved embodiments adding color to the formulation):

late) and Jeezsperse CPWS (Sunflower Seed Wax and Sodium Polyacrylate), and add directly to Water Phase.

3. Increase mixing speed to assure complete dispersion and when viscosity starts to build add, Jeechem OP (Ethylhexylpalmitate), Petroleum and Jeecide Cap 3 (Phenoxyethanol, Caprylyl Glycol, Potassium Sorbate, and Hexylene Glycol). Homogenize product 100-200 psi until uniform.

4. Add Triethanolamine until ph is uniform for top and bottom samples.

Specs: PH—5.0-6.0 TARGET 5.5. Appearance—Shiny Viscous Stringy Paste. Initial Viscosity—70,000 cps-100,000 cps TD 10 RPM. Resulted in a shiny viscous paste that molded hair for duration of time and yielded appearance of increased volume when applied to hair.

TABLE I

Example #1:
VOLUME BOOSTING MOULDING CREME (CLEAR) BASE

| Material | Weight % | Group/Function(believed function, without being bound by theory) |
|---|---|---|
| Water | 32-72%, preferably 63.3% (for Black, 61.73%; for Dark Brown 60.084%; for Lt. Brown 60.73%) | Aqueous |
| Disodium EDTA | 0.05-4%, preferably 0.2% | Sequestrant (substance that holds a mineral or metal in solution beyond its saturation point) |
| PVP (Polyvinylpyrrolidone) | 1-4%, preferably 2% | Formulation viscosity building agent: Flexibility enhancer of the gel, also applies to hold values of the product once applied to the hair |
| Vinylpyrrolidone | 1-6%, preferably 3% | Formulation viscosity building agent: Flexibility enhancer of the gel, also applies to hold values of the product once applied to the hair |
| Glycerin | 2-9%, preferably 6% | Humectant sugar alcohol that increases cellular water penetration in the hair, increasing volumized appearance. |
| Vinyl Acetate Copolymer | 1-8%, preferably 3.5% | Formulation viscosity building agent: Flexibility enhancer of the gel, also applies to hold values of the product once applied to the hair |
| Polyethlylene | 1-6%, preferably 2.5% | Several characteristics of emulsifying, thickening and synergistic bonding of waxes to hair. |
| Sodium Polyacrylate | 1-6%, preferably 2.5% | Formulation viscosity building agent. |
| Sunflower Seed Wax | 2-6%, preferably 4% | Thickening wax technology that works with disodium EDTA and Polyethlene to stick to the hair to produce a volumized look. |
| Sorbitol | 0.5-4%, preferably 1% | Humectant sugar alcohol that increases cellular water penetration in the hair, increasing volumized appearance. |
| Ethylhexylpalmitate | 5-12%, preferably 7% | Fatty acid ester that used as a carrier of the specific vinyls which effect hold of the gel. |
| Petroleum Petrolatum | 2-7%, preferably 4% | Oil base that keeps the gel from drying out the hair and produces the proper shade of shine. |
| Phenoxethanol | 0.1%-0.5%, preferably 0.2% | Preservative |
| Caprylyl Glycol | 0.1%-0.5% preferably 0.2% | Formulation stabilizer and preservative enhancer. |
| Potassium Sorbate | 0.05%-0.2%, preferably 0.1% | Preservative |
| Hexlene Glycol | 0.05%-0.3%, preferably 0.25% | Emulsion Stabilizer |
| Triethanolamine | 0.1%-0.4%, preferably 0.25% | pH Adjuster |
| Laurtrimonium Chloride | 0.2%-2% preferably 0.5% | Preservative and Emulsifier |
| Caffeine | 0.01-0.8%, preferably 0.06% | An anti DHT agent that has been shown in clinical studies to slow the effects of Male Pattern Baldness |
| Coloring Agent (see Tables hereinafter) | | |

Batching and Order of Addition:

1. Add Disodium EDTA, PVP K30 (Polyvinylpyrrolidone) together, directly to a water phase blend, WITHOUT heating. Then at the same agitation add Glycerin, add Gaffix VC-713 (Vinylacetate Copolymer), add PVP VA/W735 (Vinyl Pyrrolidone/Vinyl Acetate Copolymer/Laurtrimonium Chloride) until completely dissolved.

2. Then dry blend Caffeine, Jeezsperse CPW2 PVPKN (Polyethylene, Polyvinylpyrrolidone and Sodium Polyacry- An embodiment of the subject improved hair color formulation via volume boosting molding crème is shown below in Table II, providing a formulation that broadly comprises the materials above in addition to at least one colorant. The example below provides a black volume boosting molding crème:

Example #2

TABLE II

VOLUME BOOSTING MOULDING CRÈME BLACK: Materials of Table I
Clear crème in addition to the below materials:

| Material | Wt. % | Group/Function (believed function, without being bound by theory) |
|---|---|---|
| Charcoal Powder | 0.3-2%, preferably 1% | Natural Color |
| Dark Cocoa | 0.001-0.5%, preferably 0.003% | Natural Color |
| Instant Coffee | 0.001-0.5%, preferably 0.003% | Natural Color |

Batching and Order of Addition:
1. Add Disodium EDTA, PVP K30 (Polyvinylpyrrolidone) together, directly to a water phase blend, WITHOUT heating. Then at the same agitation add Glycerin, add Gaffix VC-713 (Vinylacetate Copolymer), add PVP VA/W735 (Vinyl Pyrrolidone/Vinyl Acetate Copolymer/Laurtrimonium Chloride) until completely dissolved.
2. Then dry blend Caffeine, Instant Coffee, Dark Cocoa, Charcoal Powder, Jeezsperse CPW2 PVPKN (Polyethylene. Polyvinylpyrrolidone and Sodium Polyacrylate) and Jeezsperse CPWS (Sunflower Seed Wax and Sodium Polyacrylate), and add directly to Water Phase.
3. Increase mixing speed to assure complete dispersion and when viscosity starts to build add, Jeechem OP (Ethylhexylpalmitate), Petroleum and Jeecide Cap 3 (Phenoxyethanol, Caprylyl Glycol, Potassium Sorbate, and Hexylene Glycol). Homogenize product 100-200 psi until uniform.
4. Add Triethanolamine until ph is uniform for top and bottom samples.
Specs: PH—5.0-6.0 TARGET 5.5; Appearance—Shiny Black Viscous Stringy Paste Initial Viscosity—70,000 cps-100,000 cps TD 10 RPM. Resulted in a shiny black viscous paste that molded hair for duration of time and yielded appearance of black colored hair (temporary) increased volume when applied to hair.

Another embodiment of the subject improved hair color formulation via volume boosting molding crème is shown below in Table III, providing a formulation that further provides a black volume boosting molding crème:

Example #3

TABLE III

VOLUME BOOSTING MOULDING CRÈME BLACK: Materials of Table I referred to herein as set forth herein below - Clear crème in addition to the below materials: Batch Size in Lbs: 2.3; Unit Size in Ounces: 32 [Batch 015152AX]

| | Material | Wt. % | Total in Units (Lbs) |
|---|---|---|---|
| A | Purified water | 94.7560% | 2.1794 |
| A | Disodium EDTA | 0.2000% | 0.0046 |
| CC | Charcoal Powder | 1% | 0.0230 |
| CC | Dark Cocoa | 0.2200% | 0.0051 |
| CC | Instant Coffee | 0.0430% | 0.0010 |
| A | Egel (Essential Ingredients) | 0.4600% | 0.0106 |
| A | Ultrez 10 Lubrizon* | 0.4500% | 0.0104 |
| A | Jeesperse CPW 4 PVPK sold by Jeen< | 0.4400% | 0.0101 |
| A | Propylene Glycol | 1.2500% | 0.0288 |
| A | cS100 Dimethicone | 0.4400% | 0.0101 |
| | Xiameter^ | | |
| A | Glydant Plus DeWolf^^ | 0.4400% | 0.0101 |
| A | Triethanolamine | 0.3000% | 0.0069 |
| A | Caffeine | 0.0010% | |
| | Total Part A | 100.0000% | 2.3000 |

*(Carbomer; a cross-linked polyacrylic acid polymer that provides efficient rheology modification with enhanced self-wetting for ease of use)

<Jeesperse CPW 4 PVPK Jeen:
Jeesperse CPW-2 PVPK-30 Styling Glue

| Phase | Ingredients | INCI Nomenclature | Supplier | % |
|---|---|---|---|---|
| A | Di Water | Di Water | | 76.80 |
| A | Dissolvine ® NA2-S | Disodium EDTA | Akzo Nobel | 0.20 |
| A | Glycerin | Glycerin | Jeen | 3.00 |
| B | Jeesperse CPW2-PVPK-30 | Polyethylene, Polyvinylpyrrolidone, Sodium Polyacyrtate | Jeen | 8.00 |
| B | JEECHEM OP | Octyl Palmitate | Jeen | 7.00 |
| B | JEECHEM HSP | Hydrolyzed Soy Protein | Jeen | 4.00 |
| C | Jeecide GII | Propylene Glycol, Dlazoildinyl Urea, Methyl Paraben, Propyl Paraben | Jeen | 1.00 |
| | | | Total | 100.00 |

Stability: RT/45C/FT
Procedure:
1) Add EDTA into the beaker containing the DI water and mix until dissolved
2) Add the rest of Phase A to the water phase
3) Add Jeesperse CPW to water phase and continue mixing
4) Once Viscosity begins to build, Add the remaining ingredients of Phase B ensuring each is dissolved before adding the next
5) Once all of Phase B is dissolved add Phase C (Jeecide GII) to the mixture and continue mixing
6) Check final pH and Viscosity SPECS
Specs
pH=5.57
Viscosity=1,390,000 cps @0.3 rpm w/Spindle #64 Using a Brookfield LV Machine.
^cS100 Dimethicone Xiameter: silicone fluid sold by Dow Corning.
^^ Glydant Plus sold by DeWolf: Glydant Plus™ is a preservative featuring a high level of antimicrobial activity in a wide variety of cosmetic and personal care formulations. Glydant Plus is also highly effective in inhibiting the growth of gram positive and gram negative bacteria, yeasts and mods without the need of additional auxiliary preservatives. This water soluble preservative has a low odor and is stable for extended periods of time over wide pH and temperature ranges. Ultra-low free formaldehyde DMDMH (<0.1%): blend of DMDMH and IPBC DMDMH.
Batching and Order of Addition:
Charge vessel with water and slowly sprinkle colors marked as CC in list, while mixing until all are fully dissolved.

Add in the following order: 1. NA2EDTA mix till fully dissolved; 2. Egel mix till fully dissolved; 3. Ultrez 10 sprinkle slowly and mix until fully dissolved; 4. Jeesperse CPW 2 PVPK sprinkle slowly and mix until fully dissolved; 5. Propylene Glycol, 6. Glydant Plus, 7. Triethanolamine, 8. Caffeine, 9. Cs100 Dimethicone. Mix ingredients in the above order.

Resulted in a shiny black viscous paste that molded hair for duration of time and yielded appearance of black colored hair (temporary) increased volume when applied to hair.

Another embodiment of the subject improved hair color formulation via volume boosting molding crème is shown below in Table IV, providing a formulation that further provides a black volume boosting molding crème:

Example #4

TABLE IV

VOLUME BOOSTING MOULDING CRÈME BLACK: Materials of Table I referred to herein as set forth herein below - Clear crème in addition to the below materials:
Batch Size in Lbs: 2.3; Unit Size in Ounces: 32 [Batch 015153AX]

|  | Material | Wt. % | Total in Units (Lbs) |
|---|---|---|---|
| A | Purified water | 91.6530% | 2.1080 |
| A | Disodium EDTA | 0.2000% | 0.0046 |
| CC | Charcoal Powder (natural colorant) | 1% | 0.0230 |
| CC | Dark Cocoa (natural colorant) | 0.0030% | 0.0001 |
| CC | Instant Coffee (natural colorant) | 0.0030% | 0.0001 |
| A | Aqua SFI Carbopol** | 0.9500% | 0.0219 |
| A | Ultrez 10 Carbopol*** | 0.4500% | 0.0104 |
| A | Egel (Essential Ingredients) | 1.7500% | 0.0403 |
| A | Jeesperse CPW 4 PVPK Jeen | 0.4400% | 0.0101 |
| A | Propylene Glycol | 1.2500% | 0.0288 |
| A | Glydant Plus DeWolf | 0.3000% | 0.0069 |
| A | Triethanolamine | 2.0000% | 0.0460 |
| A | Caffeine | 0.0010% |  |
|  | Total Part A | 100.0000% | 2.3000 |

**Aqua SFI Carbopol/Carbopol ® Aqua SF-1 Polymer; INCI Name: Acrylates Copolymer. Carbopol ® Aqua SF-1 polymer is a lightly cross-linked acrylate copolymer. It is a novel, liquid, acrylic rheology modifier designed to suspend stabilize, thicken, and enhance the appearance of surfactant-based personal cleansing products and soap-based cleansing systems.
***Ultrez 10 Carbopol: Carbopol ® Ultrez 10 Polymer; INCI Name: Carbomer; Carbopol ® Ultrez 10 polymer is a cross-linked polyacrylic acid polymer that provides efficient rheology modification with enhanced self-wetting for ease of use. Carbopol Ultrez 10 polymer can replace Carbopol ® 940 polymer and Carbopol ® 980 polymer for applications requiring easy processing and a "carbomer" INCI name, such as clear gels, hydroalcoholic gels, lotions and creams.

Batching and Order of Addition:
Charge vessel with water and slowly sprinkle colors marked as CC in list, while mixing until all are fully dissolved. Add in the following order: 1. NA2EDTA mix till fully dissolved, Aqua SFI; 2. Egel mix till fully dissolved; 3. Ultrez 10 sprinkle slowly and mix until fully dissolved; 4. Jeesperse CPW 2 PVPK sprinkle slowly and mix until fully dissolved; 5. Propylene Glycol; 6. Glydant Plus; 7. Triethanolamine; 8. Caffeine; 9. Cs100 Dimethicone. Mix ingredients in the above order.
pH range 5.2-6.3; viscosity range 140,000 to 160,000 Brookfield DV+I spindle #7 @10 RPM.
Resulted in a shiny black viscous paste that molded hair for duration of time and yielded appearance of black colored hair (temporary) increased volume when applied to hair.

Another embodiment the subject improved volume boosting molding crème is shown below in Table V, providing a formulation that broadly comprises the materials above in addition to at least one colorant. The example below provides a dark brown volume boosting molding crème:

Example #5

TABLE V

VOLUME BOOSTING MOULDING CRÈME DARK BROWN: Materials of Table I Clear crème in addition to the below materials:

| Material | Wt. % | Group/Function |
|---|---|---|
| Caramel Color | 0.02-3%, preferably 1.5% | Natural Color |
| Caramel Color Powder | 0.02-3%, preferably 1% | Natural Color |
| Dark Cocoa | 0.001-0.5%, preferably 0.003% | Natural Color |
| Instant Coffee | 0.001-0.5%, preferably 0.003% | Natural Color |
| Charcoal Powder | 0.005-0.5%, preferably 0.15% | Natural Color |

Batching and Order of Addition:
1. Add Disodium EDTA, PVP K30 (Polyvinylpyrrolidone) together, directly to a water phase blend, WITHOUT heating. Then at the same agitation add Glycerin, add Caramel Color liquid, add Gaffix VC-713 (Vinylacetate Copolymer), add PVP VA/W735 (Vinyl Pyrrolidone/Vinyl Acetate Copolymer/Laurtrimonium Chloride) until completely dissolved.
2. Then dry blend Caffeine, Caramel Color Powder, Dark Cocoa, Instant Coffee, Charcoal Powder Jeezsperse CPW2 PVPKN (Polyethylene, Polyvinylpyrrolidone and Sodium Polyacrylate) and Jeezsperse CPWS (Sunflower Seed Wax and Sodium Polyacrylate), and add directly to Water Phase.
3. Increase mixing speed to assure complete dispersion and when viscosity starts to build add, Jeechem OP (Ethylhexylpalmitate), Petroleum and Jeecide Cap 3 (Phenoxyethanol, Caprylyl Glycol, Potassium Sorbate, and Hexylene Glycol). Homogenize product 100-200 psi until uniform.
Specs: PH—5.0-6.0 TARGET 5.5; Appearance—Shiny Dark Brown Viscous Stringy Paste
Initial Viscosity—70,000 cps-100,000 cps TD 10 RPM.
Resulted in a shiny dark brown viscous paste that molded hair for duration of time and yielded appearance of black colored hair (temporary) increased volume when applied to hair.

Another embodiment the subject improved volume boosting molding crème is shown below in Table VI, providing a dark brown volume boosting molding crème:

Example #6

TABLE VI

VOLUME BOOSTING MOULDING CRÈME DARK BROWN: Materials of Table I referred to herein as set forth herein below - Clear crème in addition to the below materials:
Batch Size in Lbs: 2.3; Unit Size in Ounces: 32 [Batch 015154AX]

|  | Material | Wt. % | Total in Units (Lbs) |
|---|---|---|---|
| A | Purified water | 89.5630% | 2.0599 |
| A | Disodium EDTA | 0.2000% | 0.0046 |
| CC | liquid Caramel Color | 1.5000% | 0.0345 |
| CC | Caramel Color Powder | 1.0000% | 0.0230 |
| CC | Dark Cocoa | 0.0030% | 0.0001 |
| CC | Charcoal Powder (natural colorant) | 0.1500% | 0.0035 |
| CC | Instant Coffee (natural colorant) | 0.0030% | 0.0001 |
| A | Aqua SFI Carbopol | 0.9500% | 0.0219 |
| A | Ultrez 10 Carbopol | 0.4500% | 0.0104 |
| A | Egel Essential | 1.7500% |  |

TABLE VI-continued

VOLUME BOOSTING MOULDING CRÈME DARK BROWN:
Materials of Table I referred to herein as set forth herein below -
Clear crème in addition to the below materials:
Batch Size in Lbs: 2.3; Unit Size in Ounces: 32 [Batch 015154AX]

|   | Material | Wt. % | Total in Units (Lbs) |
|---|---|---|---|
|   | Ingredients |   |   |
| A | Jeesperse CPW 2 PVPK3 Jeen | 0.4400% |   |
| A | Propylene Glycol | 1.2500% |   |
| A | cS100 Dimethicone Xiameter | 0.4400% | 0.0101 |
| A | Glydant Plus | 0.3000% | 0.0069 |
| A | Triethanolamine | 2.0000% | 0.0460 |
| A | Caffeine | 0.0010% |   |
|   | TOTAL PART A | 100.0000% | 2.2209 |

Batching and Order of Addition:
Charge vessel with water and slowly sprinkle colors marked as CC above while mixing until all are fully dissolved. Add all other items in order per above while mixing, sprinkle all powders slowly into mix, mix until all are in a complete gel. Result: pH range 5.2-6.3; viscosity range 140,000 to 160,000 Brookfield DV+I spindle #7 @10 RPM.

Another embodiment the subject improved volume boosting molding crème is shown below in Table VII, providing a formulation that broadly comprises the materials above in addition to at least one colorant. The example below provides a light brown volume boosting molding crème:

Example #7

TABLE VII

VOLUME BOOSTING MOULDING CRÈME LIGHT BROWN:
Materials of Table I Clear crème in addition to the below materials:

| Material | Weight % | Group/Function |
|---|---|---|
| Caramel Color | 0.02-3%, preferably 1.2% | Natural Color |
| Caramel Color Powder | 0.02-3%, preferably 0.8% | Natural Color |
| Dark Cocoa | 0.001-0.5%, preferably 0.003% | Natural Color |
| Instant Coffee | 0.001-0.5%, preferably 0.003% | Natural Color |

Batching and Order of Addition:
1. Add Disodium EDTA, PVP K30 (Polyvinylpyrrolidone) together, directly to a water phase blend, WITHOUT heating. Then at the same agitation add Glycerin, add Caramel Color liquid, add Gaffix VC-713 (Vinylacetate Copolymer), add PVP VA/W735 (Vinyl Pyrrolidone/Vinyl Acetate Copolymer/Laurtrimonium Chloride) until completely dissolved.
2. Then dry blend Caffeine, Caramel Color Powder, Dark Cocoa, Instant Coffee, Jeezsperse CPW2 PVPKN (Polyethylene, Polyvinylpyrrolidone and Sodium Polyacrylate) and Jeezsperse CPWS (Sunflower Seed Wax and Sodium Polyacrylate), and add directly to Water Phase.
3. Increase mixing speed to assure complete dispersion and when viscosity starts to build add, Jeechem OP (Ethylhexylpalmitate), Petroleum and Jeecide Cap 3 (Phenoxyethanol, Caprylyl Glycol, Potassium Sorbate, and Hexylene Glycol). Homogenize product 100-200 psi until uniform.
4. Add Triethanolamine until ph is uniform for top and bottom samples.
Specs: PH—5.0-6.0 TARGET 5.5. Appearance—Shiny Lt Brown Viscous Stringy Paste. Initial Viscosity—70,000 cps-100,000 cps TD 10 RPM. Resulted in a shiny light brown viscous paste that molded hair for duration of time and yielded appearance of black colored hair (temporary) increased volume when applied to hair.

Another embodiment the subject improved volume boosting molding crème is shown below in Table VIII, providing a light brown volume boosting molding crème:

Example #8

TABLE VIII

VOLUME BOOSTING MOULDING CRÈME LIGHT BROWN:
Materials of Table I referred to herein as set forth herein below -
Clear crème in addition to the below materials:
Batch Size in Lbs: 2.3; Unit Size in Ounces: 32 [Batch 015155AX]

|   | Material | Wt. % | Total in Units (Lbs) |
|---|---|---|---|
| A | Purified water | 90.2130% | 2.0749 |
| A | Disodium EDTA | 0.2000% | 0.0046 |
| CC | liquid Caramel Color | 1.2000% | 0.0276 |
| CC | Caramel Color Powder | 0.8000% | 0.0184 |
| CC | Dark Cocoa | 0.0030% | 0.0001 |
| CC | Instant Coffee (natural colorant) | 0.0030% | 0.0001 |
| A | Aqua SFI Carbopol | 0.9500% | 0.0219 |
| A | Ultrez 10 Carbopol | 0.4500% | 0.0104 |
| A | Egel Essential Ingredients | 1.7500% | 0.0403 |
| A | Jeesperse CPW 2 PVPK3 Jeen | 0.4400% | 1.0101 |
| A | Propylene Glycol | 1.2500% | 0.0288 |
| A | cS100 Dimethicone Xiameter | 0.4400% | 0.0101 |
| A | Glydant Plus DeWolf | 0.3000% | 0.0069 |
| A | Triethanolamine | 2.0000% | 0.0460 |
| A | Caffeine | 0.0010% |   |
|   | TOTAL PART A | 100.0000% | 2.3 |

Batching and Order of Addition:
Charge vessel with water and slowly sprinkle colors marked as CC above while mixing until all are fully dissolved. While mixing, add all powders and ingredients very slowly and continue to mix following the above order until all are fully formed into a gel
Result: viscosity range 140,000 to 160,000 Brookfield DV+I spindle #7 @10 RPM.

Preferable embodiments include addition of colorants, and more preferably natural colorants. Each set of elements, provides different functions to the formulation. Hydrocarbons preferably include petroleum compounds. Thickening agents preferably include cetyl alcohol and Sodium Polyacrylate Sunflower Seed Wax, for example; humectants may be for example a glycerol, glycerin, disodium EDTA, Sorbito, etc.; emollients are preferably a combination of waxes. Waxes contemplated include carnuba wax, cetyl esters wax, emulsifying wax, methylparaben, and ethylparaben. In addition to keratin fibers, oat fiber may be used in the composition. Emollients may further include at least one fatty acid ester Fatty acids include, but are not limited to simple esters with lower chain alcohols (methyl-, ethyl-, n-propyl-, isopropyl- and butyl esters). Preservatives, colorants and male pattern baldness treatments may be added to the composition.

Thickening agents preferably include cetyl alcohol and Sodium Polyacrylate Sunflower Seed Wax, for example; humectants may be for example a glycerol, glycerin, disodium EDTA, Sorbito, etc.; emollients are preferably a combination of waxes. Waxes contemplated include carnuba wax, cetyl esters wax, emulsifying wax, methylparaben, and ethylparaben. In addition to keratin fibers, oat fiber may be used in the composition. Emollients may further include at least one fatty acid ester Fatty acids include, but are not limited to simple esters with lower chain alcohols (methyl-, ethyl-, n-propyl-, isopropyl- and butyl esters). Preservatives, colorants and male pattern baldness treatments may be added to the composition.

The forgoing example formulations provides a hair paste particularly geared toward men (use by women is contemplated) that provides volume boosting molding properties, as well as temporary color treatment for the hair.

The foregoing descriptions of specific embodiments of the present disclosure have been presented for purposes of illustration and description. They are not intended to be exhaustive or to limit the present disclosure to the precise forms disclosed, and obviously many modifications and variations are possible in light of the above teaching. The exemplary embodiment was chosen and described in order to best explain the principles of the present disclosure and its practical application, to thereby enable others skilled in the art to best utilize the present disclosure and various embodiments with various modifications as are suited to the particular use contemplated. These embodiments, as well as additional changes and modifications may suggest themselves to one skilled in the art, all falling within the scope of the invention as defined by the subjoined claims.

What is claimed is:

1. A hair styling formulation consisting of:
   a. a natural color agent consisting of coffee, present in an amount ranging from 0.001-0.5 wt. % of the composition, said coffee containing caffeine that provides anti-dihydrotestosterone (D.H.T.) effects and providing a hair color treatment that stains the hair brown, dark brown or black;
   b. a viscosity building agent selected from the group consisting of 1-4% by weight vinylpyrrolidone (PVP), 1-6% by weight vinylpyrrolidone, 1-8% by weight vinyl acetate copolymer, 1-6% by weight sodium polyacrylate or combinations thereof;
   c. a thickening agent from 2-14% by weight of the composition selected from the group consisting of sunflower seed wax, cetyl alcohol and combinations thereof;
   d. said hair styling formulation being a leave-in hair product for molding and volumizing the hair
   e.
   f.
   g.

2. The hair styling formulation of claim 1, wherein said hair products are hair styling products selected from a group consisting of gels, crèmes, sprays, mousses, and pomades.

3. A hair styling formulation consisting of an aqueous emulsion and at least one of each of the following: i) coffee containing caffeine for providing anti-dihydrotestosterone (D.H.T.) effects by stimulating hair growth, ii) disodium EDTA, iii) carbomer, iv) styling glue consisting of Di water, disodium EDTA, glycerin, polyethylene, polyvinylpoyroolidone sodium polyacrylate, octyl palmitate, hydrolyzed soy protein, propylene glycol, dlazoildinyl urea, methyl paraben and propyl paraben, v) hexylene glycol, vi) 100 cS dimethicone, vii) a viscosity building agent selected from the group consisting of 1-4% by weight polyvinylpyrrolidone (PVP), 1-6% by weight vinylpyrrolidone, 1-8% by weight vinyl acetate copolymer, 1-6% by weight sodium polyacrylate; or combinations thereof, and viii) a thickening agent from 2-14% by weight of the composition selected from the group consisting of sunflower seed wax, cetyl alcohol and combinations thereof; wherein said hair styling formulation is a leave-in hair product that for molding and volumizing the hair.

\* \* \* \* \*